United States Patent [19]

Jacobi

[11] Patent Number: 4,971,558

[45] Date of Patent: Nov. 20, 1990

[54] PORCELAIN INLAY FORMED DIRECTLY IN A CAVITY AND METHOD FOR MAKING SAME

[75] Inventor: Richard Jacobi, Midwest City, Okla.

[73] Assignee: Board of Regents of the University of Oklahoma, Norman, Okla.

[21] Appl. No.: 175,096

[22] Filed: Mar. 30, 1988

[51] Int. Cl.$^5$ .............................................. A61C 5/04
[52] U.S. Cl. .................................................. 433/226
[58] Field of Search ...................... 433/228.1, 226, 229; 264/16

[56] References Cited

U.S. PATENT DOCUMENTS

| | | | |
|---|---|---|---|
| 983,579 | 2/1911 | Taggart | 433/226 X |
| 1,211,244 | 1/1917 | Schroeder et al. | 433/226 |
| 2,317,008 | 4/1943 | Werner | 264/16 |
| 4,378,248 | 3/1983 | Griffith | 433/228.1 X |
| 4,500,288 | 2/1985 | von Weissenfluh | 433/226 X |
| 4,557,691 | 12/1985 | Martin et al. | 433/228.1 X |
| 4,604,059 | 8/1986 | Klaus et al. | 433/228.1 X |
| 4,654,007 | 3/1987 | Sigler et al. | 433/226 |
| 4,685,969 | 8/1987 | Schmid et al. | 433/228.1 X |
| 4,696,646 | 9/1987 | Maitland | 433/229 X |
| 4,726,770 | 2/1988 | Kurer | 433/229 |

OTHER PUBLICATIONS

Skinner, "Dental Porcelains: Compositions and Condensation", The Science of Dental Materials, 3d ed., W. B. Saunders Co., Phila., p. 119, (1953).
Toogood et al., "Technique for Establishing Porcelain Margins", J. Pros. Dentistry, 40(4):464-465, (1978).
Vryonis, "A Simplified Approach to the Complete Porcelain Margin", J. Prosthetic Dentistry, 42(5):592-593, (1979).
Prince et al., "The All-porcelain Labial Margin for Ceramometal Restorations: A New Concept", J. Pros. Dentistry, 50(6):793-796, (1983).
Pinnell et al., "Light-cured Porcelain Margins: A New Technique", J. Pros. Dentistry, 58(1):50-52, (1987).
"Brilliant D.I., Direct-Inlay-System", Coltene brochure (date unknown), 7 pages.
"Something to Smile About", Coltene brochure (date unknown), 2 pages.
"Spectrum", Dentsply brochure (date unknown), 2 pages.
"Direct Porcelain Repair" handout distributed at OU College of Dentistry 3-27-87 and at the Oklahoma Dental Assn. meeting 4-23-87, 2 pages.

Primary Examiner—John J. Wilson
Assistant Examiner—Nicholas D. Lucchesi
Attorney, Agent, or Firm—Dunlap, Codding, Peterson & Lee

[57] ABSTRACT

A heat fused porcelain inlay formed directly in a cavity in a patient's mouth and method for making same comprising a mixture of a porcelain and a binding agent, preferably a resin. The mixture is placed in the cavity and cured therein. The cured mixture is placed in an oven to heat fuse the porcelain and burn off at least a portion of the binding agent resulting in a ceramic core. Corrective layers of the mixture may be added to the ceramic core with subsequent curing and heat-fusing. One embodiment comprises disposing a framework in the mixture prior to curing. A kit comprising a supply of porcelain and binding agent for use in making dental inlays.

13 Claims, 2 Drawing Sheets

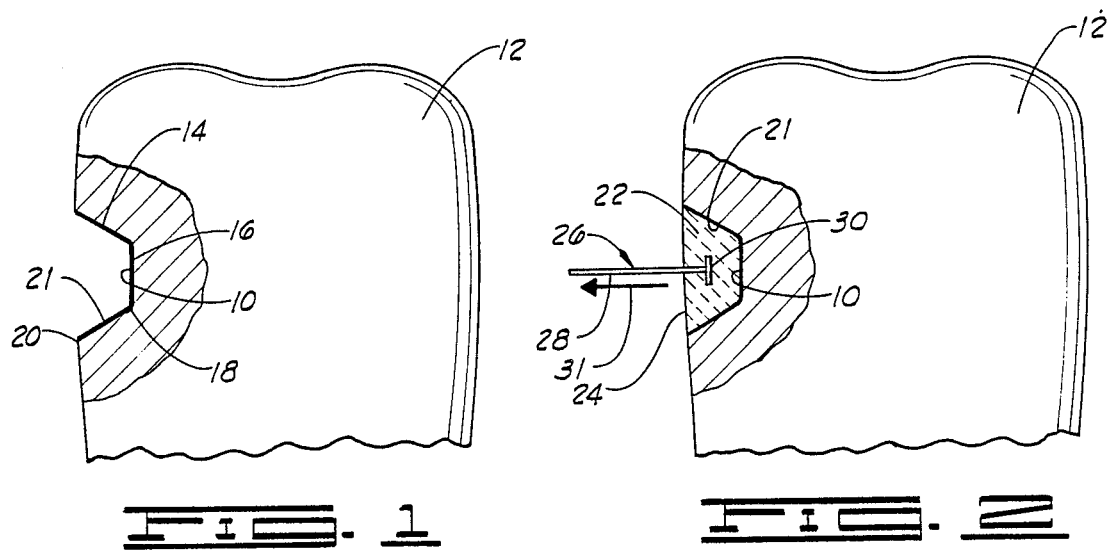
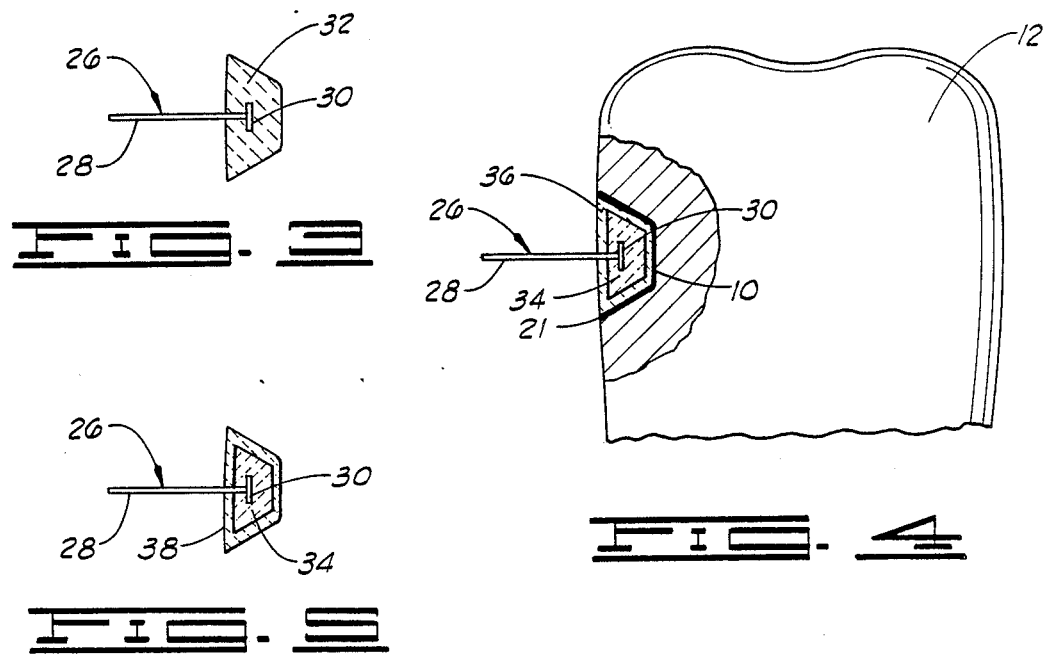

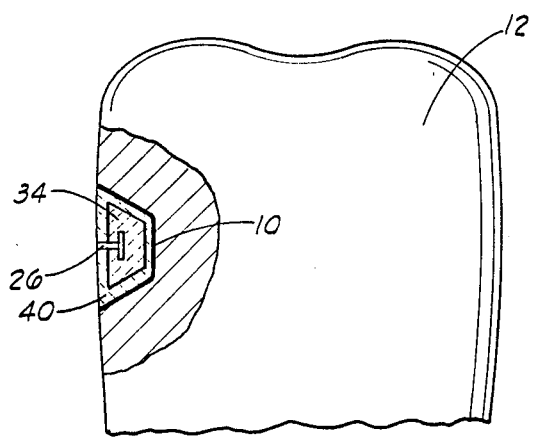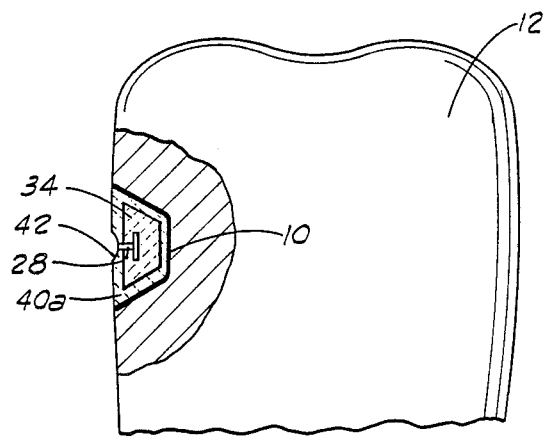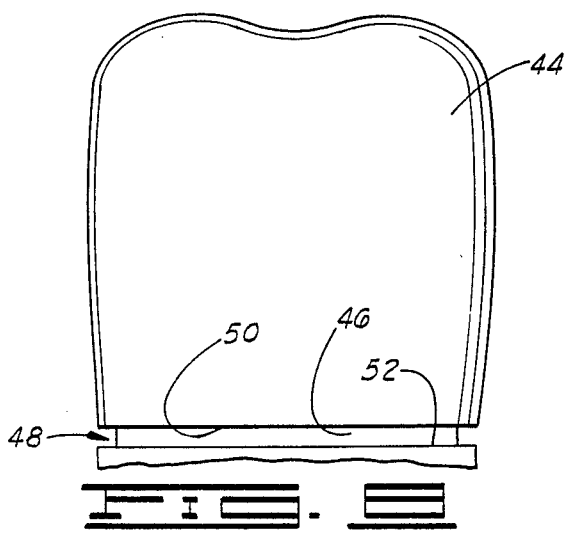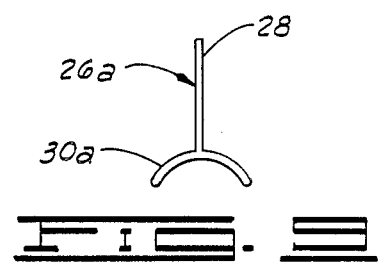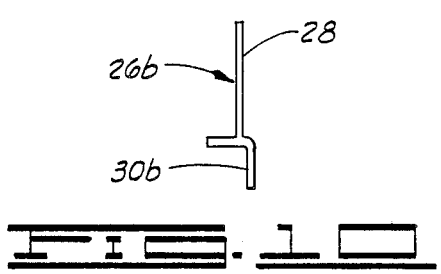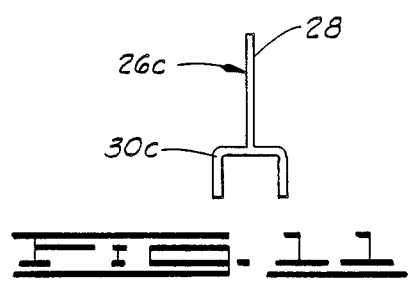

PORCELAIN INLAY FORMED DIRECTLY IN A CAVITY AND METHOD FOR MAKING SAME

FIELD OF THE INVENTION

The present invention relates generally to dental fillings and, more particularly, but not by way of limitation, the present invention relates to a method for forming a ceramic inlay and a framework which may be used with such inlay or other types of inlays.

BRIEF DESCRIPTION OF THE DRAWINGS

FIG. 1 is a diagrammatic view of a tooth with a cavity formed therein and a separating agent disposed in the cavity.

FIG. 2 is a diagrammatic view of the tooth of FIG. 1 showing a sectional view of a mixture comprised in accordance with the present invention disposed therein.

FIG. 3 is a sectional view of the cured mixture (mixture inlay) formed in the cavity as shown in FIG. 2 and removed from the cavity.

FIG. 4 is a view of a tooth with a sectional view showing a ceramic core formed from the mixture inlay disposed in the cavity with a corrective layer comprised in accordance with the present invention disposed in the cavity in the tooth and generally about the ceramic core.

FIG. 5 is a sectional view of the ceramic core and a corrective ceramic layer formed from the corrective layer disposed generally about the ceramic core.

FIG. 6 is a view of a tooth with a sectional view of the ceramic inlay comprised of the ceramic core and a corrective ceramic layer formed from the corrective layer disposed and cemented in the cavity.

FIG. 7 is a view of a tooth with a sectional view showing a modified corrective ceramic layer formed about the ceramic core and disposed in the cavity.

FIG. 8 is an elevational view of a crown disposed on a tooth with a lower end of the crown disposed above a shoulder formed on the tooth thereby forming a marginal gap or cavity generally between the lower end of the crown and the shoulder.

FIG. 9 is a side elevational view of a modified framework.

FIG. 10 is a side elevational view of another modified framework.

FIG. 11 is a side elevational view of yet another modified framework.

DETAILED DESCRIPTION OF THE PREFERRED EMBODIMENTS

Porcelain was developed for use in teeth many years ago to provide a hard, wear-resistant replacement for lost tooth structure. Porcelain inlays have not been used extensively in dentistry, however, due to the weak cement line and the extensive laboratory procedure required for fabrication.

A zinc phosphate cement which has been used for years to occupy the gap between the cavity wall and the porcelain was aesthetically unpleasing and gradually washed out, leaving the tooth susceptible to recurrent decay. Some recently developed methods for securing a porcelain inlay in a tooth have made the porcelain inlay a more viable and aesthetic alternative to the currently used amalgam fillings. Now what is needed is a method to obviate the need for the expensive, time consuming laboratory work previously associated with porcelain inlays.

In the past, the process used to make a heat-fused porcelain inlay way was a complicated and expensive procedure. The dentist took an impression of the cavity and sent it or a dental stone die made therefrom to the lab. A temporary filling was placed in the cavity in the patient's mouth. Since dental stone will not withstand the temperatures required to fuse porcelain, a refractory die was prepared. The cavity in the refractory die was filled with a mixture of porcelain and modeling fluid, usually water, and placed in an oven. After heat-fusion of the porcelain occured, the refractory die was removed by sandblasting. Corrections and staining required subsequent firings in the oven.

The finished inlay was returned to the dentist. If the inlay did not fit properly, the inlay and a new impression or dental stone die was sent back to the laboratory. Similarly, when ceramometal crowns received from the laboratory were too short, the crown had to be sent back to the laboratory so that the proper corrections could be made.

It can be appreciated from the foregoing that, in the past, several patient appointments with the dentist were commonly required and laboratory fees could be expensive. The present invention provides a method for using the cavity itself as a mold for producing heat-fused porcelain inlays thereby providing the dentist with a convenient means for producing a porcelain inlay generally in one patient visit.

In practicing the present invention, a cavity 10 first is prepared in a tooth 12 to be filled, as shown in FIG. 1. The cavity 10 is formed by the dentist in a manner well known in the art to remove decayed tooth material and form the cavity 10 sized and shaped to receive a filling. The cavity 10 is formed by shaping sidewall 14 in the tooth 12 which extends a distance into the tooth 12 and which is tapered inwardly from the face of the tooth 12 to a lower end 16 of the cavity 10. The inward taper of the sidewall 14 facilitates the removal of the inlay at various stages of the process of the present invention, as will be described in greater detail below. A corner 18 is formed between the sidewall 14 and the lower end 16 of the cavity 10 and, preferably, the corner 18 is rounded. An edge 20 is formed between the sidewall 14 and the face of the tooth 12 and the edge 20 preferrably is formed at a substantially sharp angle, not rounded, to prevent the formation of thin layers of mixture being formed during the making of the inlay and in the final inlay constructed in accordance with the present invention, as will be described in greater detail below.

After the cavity 10 has been formed, the cavity 10 is coated with a separating agent 21, as shown in FIG. 1. Suitable separating agents comprise petroleum jelly or vinyl polysiloxane, one suitable vinyl polysiloxane being commercially available as Reprosil, low viscosity or light bodied sold by Caulk/Dentsply of Milford, Del. The separating agent 22 serves to facilitate removal of the cured mixture from the cavity 10 in a manner to be described in greater detail below. The separating agent 22 preferably is applied to the cavity 10 with a spatula in excess and a stream of air applied thereto to form a thin layer of the separating agent 21 over the entire surface of the cavity 10.

A quantity of a mixture 22 is prepared and the mixture 22 is disposed in the cavity 10, as shown in FIG. 2, preferably sufficient to fill the cavity 10 in order to conform to the desired configuration of the tooth 12. At this stage, the cavity 10 may be overfilled with the mixture 22 in order to compensate for any heat shrinkage that occurs during the heating step, discussed below.

The mixture 22 comprises a mixture of a dental porcelain and a binding agent. The dental porcelain used at this stage of the procedure is in a powder form which fuses at a relatively high temperature such as 1170° C. As presently commercially available, porcelain of this type has the advantage of incurring less shrinkage during the fusing step and, as fused, provides a stronger structure, as compared to porcelains having lesser curing temperatures. This particular porcelain thus provides a preferred material. However, this type of porcelain usually has an opaque coloring which is not as natural looking as porcelains having lesser fusing temperatures and, thus, from an esthetic veiwpoint, this type of porcelain is not used to form the outer periphery of the inlay constructed in accordance with the present invention.

A dental porcelain of the type just described is commercially available from Vita Zahnfrabrik GmbH, Bad Sackingen, West Germany, distributed by Vident, Inc. under the name Hi Ceram Core Material. Another commercially available porcelain, VMK 68, also is available in a form having a lower fusing temperature which is prefered to form corrective ceramic layer to be described below. This particular procelain will bind to metal which is a consideration when designing the framework (to be described below). If the framework (to be described below) is constructed of a porcelain, it is preferred to use a porcelain capable of binding to itself and such a pocelain is commercially available from this same company under the name Vitadur N.

The binding agent serves to bind the porcelain prior to firing. Binding agents can be of the type which are commonly referred to as light cured or chemically cured. If chemically cured, the mixture of porcelain and binding agent will cure or set with the passage of time due to the chemical reactions therebetween. If light cured, the mixture of porcelain and binding agent will cure or set after exposure to light, white or ultraviolet. A chemically cured binding agent suitable for use in the present invention is a resin bis-GMA commercially available from Johnson and Johnson. A light cured binding agent suitable for use in the present invention is a resin bis-GMA commercially available from Caulk/Dentsply of Milford, Del. To form the ceramic core, the chemically cured binding agent is preferred. The binding agent must be suitable for use in a patient's mouth, non-toxic. Preferably, the binding agent should burn out cleanly and not leave an ash residue which would discolor the porcelain.

In general, the less binding agent in the mixture, the stronger the resulting cured porcelain structure. A ratio of about 2.5 to about 1.0 by weight porcelain to binding agent has been found to form a thick paste suitable for use in the present invention. Any ratio may be used which forms a workable consistency. It is, however, advantageous to use as little of the binding agent as possible since the presence of the binding agent may contribute to the degree of heat-shrinkage.

After the mixture 22 has been disposed in the cavity 10, excess binding agent is removed from the mixture 22 by blotting an external surface 24 of the mixture 22 in the cavity 10 with an absorbent material such as cotton. Excess resin will tend to soak into the cotton. The procedure of the present invention will work without this blotting step, except there will be more shrinkage of the porcelain, the porcelain will tend to be weaker and the resulting porcelain will be more opaque, less esthetically pleasing.

Once the mixture 20 is in the cavity 10 in the proper amount and configuration, the mixture 20 is permitted to cure. If a chemical cure is required by the selection of the binding agent, waiting the appropriate amount of time will serve to cure or set the mixture 22. For example, if the binding agent is the Hi Ceram Core Material about four minutes is required for the chemical cure to be effected in order for the mixture 22 to be stabilized and set so the mixture 22 substantially will retain its shape as formed in the cavity 10. If the choice of the binding agent requires a light cure, the mixture 22 is exposed to an appropriate light source for a sufficient amount of time to cure the mixture 22. The curing of the mixture 22 stabilizes the mixture 22 sufficiently such that the mixture 22 can be removed from the cavity 10 and still basically retain the shape formed in the cavity 10. As mentioned before, a chemically cured type of binding agent is preferred at the stage of the procedures for creating the ceramic core.

Before the mixture 22 is cured in the cavity 10, a framework 26 is disposed or inserted into the mixture 22. The framework 26 can be inserted into the cavity 10 before the mixture 22 is placed in the cavity 10. The framework 26 can be formed from any material that can withstand the high temperatures required to heat-fuse the porcelain and which will bind to the porcelain. The framework 26 preferably is made from a high fusing porcelain or metal which is bondable to the mixture 22, such as aluminum oxide or a nickel-chrome alloy, for example. The framework 26 must be constructed of a material which is resistant at temperatures at which porcelain is fused. By using the framework 26, less mixture 22 is used to fill the cavity 10 since a portion of the cavity 10 space is occupied by a portion of the framework 26 and thus less binding agent will be present. This will result in a decrease in the degree of heat shrinkage and increase in the strength of the resulting porcelain inlay.

As shown in FIGS. 2, 3, 4 and 5, the framework 26 has a handle 28 and a base 30. The base 30 is connected to one end of the handle 28, and the handle 28 extends a distance from the base 30. The base 30 is contoured roughly to the shape of the cavity 10.

In operation, the base 30 is disposed in the mixture 22 with a portion of the handle 28 extending a distance from the external surface 24 of the mixture 22.

After the mixture 22 is cured in the cavity 10, the cured mixture is removed from the cavity 10 by gripping the handle 28 and pulling the handle 28 in a direction 31 to remove the cured mixture from the cavity 10. The cured mixture is sometimes referred to herein as the mixture inlay and the mixture inlay is shown in FIG. 3 removed from the cavity 10, the mixture inlay being designated in FIG. 3 by the general reference numeral 32.

The mixture inlay 32 may be trimmed at this point in the procedure to remove any excess and get rid of the flash. The mixture inlay 32 could be trimmed while the mixture inlay 32 still is in the cavity 10 or after the mixture inlay 32 has been removed from the cavity 10. It should be noted that it is acceptable if the mixture inlay 32 is underfilled in the sense that it does not completely fill the cavity 10 at this stage of the procedure.

The mixture inlay 25 is placed in a glazing oven (not shown) for a sufficient amount of time and at a sufficient temperature for at least a portion of the binding agent to burn off and for the porcelain to heat fuse. Any oven that can achieve and maintain the appropriate temperatures may be used.

If the temperature is too high, the porcelain will bind prematurely thereby unnecessarily trapping binding agents which results in discloration and a possible loss of strength. Preferably, the mixture inlay 32 first is heated to a temperature above the kindling temperature of the resin, but below the fusion temperature of the porcelain for a period of time sufficient to burn off as much of the binding agent as possible. For example, 600° C. for two minutes has been found to be sufficient to burn off a significant amount of the binding agent bis-GMA in a mixture with VMK 68 porcelain or Hi Ceram Core Material. The time will vary with the size of the mixture inlay 32 with larger sizes requiring more time. In general, the mixture inlay 32 is left in the oven until the mixture inlay 32 turns white before the temperature is raised to the fusing temperature of the ceramic.

The mixture inlay 32 then is heated to at least the fusion temperature of the porcelain for a period of time sufficient to heat fuse the porcelain. For example, 1100° C. for two minutes has been found to be sufficient for the Hi Ceram Core Material with a corresponding fusion temperature. Over-heating can cause a distortion of the porcelain and should therefore be avoided. Again, the time required to heat fuse the mixture inlay 32 varies with the size of the mixture inlay 32 with larger sizes requiring more time.

The heat-fused mixture inlay 32 formed is a ceramic core 34 (shown in FIGS. 4 and 5). The ceramic core 34 is cooled and placed in the cavity 10.

If the cavity 10 initially was over-filled with the mixture 22 or is small, the ceramic core 34 may be the appropriate size. In this instance, the ceramic core 34 comprises the porcelain inlay and the ceramic core 34 is cemented into the cavity 10.

In most instances, the mixture inlay 22 shrinks in the forming of the ceramic core 34 and thus the ceramic core 34 will be undersized with respect to filling the cavity 10. The ceramic core 34 is gripped by the handle 28 and placed in the cavity 10. If it is determined that the ceramic core 34 is undersized, at least one application of a corrective layer of porcelain and binding agent is applied to achieve the desired configuration.

The ceramic core 34 is removed from the cavity 10. If the separating agent 21 has been removed from the cavity 10, a new layer of separating agent 21 is applied to the cavity 10 in the manner described before and as shown in FIG. 4.

A corrective layer then is prepared. The corrective layer comprises porcelain and binding agent. The binding agent is the same type of binding agent described before with respect to the mixture 22. The porcelain has a lower fusion temperature as compared to the porcelain used in the mixture 22 so the corrective layer will fuse at a lower temperature as compared to the mixture 22 to prevent distorting the ceramic core 34. In one embodiment, the porcelain VMK 68, distributed by Vident, Inc., was used in the corrective layer mixture with a fusion temperature of about 960° C. along with the same resin or binding agent as described before with respect to the mixture 22.

The corrective layer is disposed in the cavity 10, as illustrated in FIG. 4 with the corrective layer being designated by the general reference numeral 36 in FIG. 4. The ceramic core 34 then is disposed in the cavity 10 and generally on the corrective layer 36. This will force excess corrective layer 36 out from the cavity 10. The exposed surface of the ceramic core 34 also is covered with corrective layer 36 and excess binding agent is removed as described before.

Once the corrective layer 36 is cured, the excess corrective layer 36 will be bonded to the ceramic core 34. The cured corrective layer 36 sometimes is referred to herein as the cured corrective layer and the cured corrective layer is designated in FIGS. 5 and 6 by the general reference numeral 38.

The cured corrective layer 38 may be formed by first inserting the ceramic core 34 into the recess 10 and then inserting and packing the corrective layer 36 around the ceramic core 34. This procedure probably would result in a void generally between the ceramic core 34 and the lower end 16 portion of the cavity 10 and generally between the ceramic core 34 and portions of the sidewall 14 generally near the lower end 16 of the cavity 10. However, this should be acceptable in most instance since this void will not affect the acceptability of the resulting inlay from a strength or esthetic veiwpoint.

The cured corrective layer 38 along with the ceramic core 34 is removed from the cavity 10 by gripping the handle 28 and pulling the handle 28 in the direction 31. The cured corrective layer 38 along with the ceramic core 34 is placed in an oven and heated at a temperature of about 600° Centigrade for about two minuties to burn out the resin and then heat fused at a temperature of about 960° Centigrade. The heat fused cured corrective layer 38 sometimes is referred to herein as the corrective ceramic layer and the corrective ceramic layer is shown in FIG. 6 and designated therein by the general reference numeral 40.

Although it may be necessary to add additional layers in some applications, assuming the ceramic core 34 and corrective ceramic layer 40 now fit the cavity 10, the separating agent 21 is removed from the cavity 10, and the porcelain inlay comprising the ceramic core 34 and the corrective ceramic layer 40 are cemented in the cavity 10, as illustrated in FIG. 6.

After the ceramic core 34 and corrective ceramic layer 40 have been cemented into the cavity 10, the handle 28 of the framework 26 is cutoff generally at the external surface formed by the corrective ceramic layer 40, as shown in FIG. 5. If the framework 26 is constructed of a metallic material, this will leave a small circularly shaped area of different material on the external surface of the corrective ceramic layer 40. If the framework 26 is constructed of a ceramic material, this circularly shaped area should not present an esthetic problem of any significance.

One solution to this potential problem is to underfill a portion of the corrective ceramic layer 40 generally about the handle 28 to form a depression 42 in the exterior surface of the corrective ceramic layer 40 generally about the handle 28, as shown in FIG. 7. The handle 28 then is cut from the framework 26 at the surface of the depression 34. The depression 34 then can be filled with a mixture of porcelain and binding agent and cured and heat fused in a manner described before with respect to the corrective ceramic layer 40.

Preferably, these portions of the ceramic core 34 and corrective ceramic layer 40 which contact the cavity 10 are roughened to promote a better contact for cementing therebetween. The roughening step may be accomplished by sandblasting or etching with acid the cavity-contacting portions of the ceramic core 34 and corrective ceramic layer 40 bonded thereto.

A low fusing glaze 44, such as Ceramco by Johnson & Johnson Co. of the East Windsor, N.H., may be applied to the external surface 40 of the porcelain inlay to fill any porosity and produce a smooth surface. Also, a stain may be added to this glaze.

Although only one type of cavity 10 has been illustrated in the drawings, the present invention may be utilized to form porcelain inlays for any type of cavity regardless of size or location on or about the tooth to be filled.

Porcelain margins on porcelain-fused-to-metal crowns have become increasingly popular in recent years. Until their development, dentists were faced with the dilemma of either displaying an unsightly metal collar at the gingival margin or placing the margin deeply enough subgingival to be hidden from view, with the attendant risk of gingival inflammation.

Various methods have been developed for forming porcelain margins in the laboratory. Some of these involve firing part of the porcelain veneer, filling the shrinkage gap at the shoulder with porcelain mixed with conventional fluid, removing the crown from the die, then re-filing. Also in the past, a method for filling the margin with a mixture of porcelain and wax has been used, which is less likely to fracture as the crown is lifted from the die.

In spite of these efforts, the porcelain margins of some crowns are found to be short when tried in the patient's mouth. Until now, the only course open for the conscientious dentist faced with this situation was to make another impression, pour a new dye, and return these to the laboratory for the addition of more porcelain. The present invention provides a method for forming a porcelain additiona (inlay) for filling gingival margin gap (referred to herein as cavities).

As shown in FIG. 8, a crown 44 is placed on the remaining portion of a patient's tooth 46 and a marginal gap or cavity 48 exist between a lower end 50 of the crown 44 and a shoulder 52 formed on the prepared tooth 46.

A mixture is prepared in accordance with the present invention exactly as described before with respect to the mixture 22. In this particular embodiment, it is preferred to use a light curing bis-GMA resin, such as Vita shoulder porcelain, commercially available from Vita Zahnfrabrik GmbH, Bad Sackingen, West Germany in a ratio with the porcelain of approximately 2.5 to about 1.0 by weight porcelain to resin to form a thick paste, the thick paste comprising the mixture 22.

The separating agent then is applied to the tooth 56 surface. All visible excess separating agent then is removed with a cotton pellet.

The mixture is added or disposed in the cavity 48 in slight excess of the cavity 48.

After the mixture has been added to the cavity 48, the crown 44 is seated firmly. Excess resin is removed from the mixture by blotting firmly with cotton in the manner described before.

Excess mixture is removed with a plastic or stainless steel instrument. A slight over contour is left to compensate for shrinkage.

A light is applied to the mixture to cure the mixture, the light being applied to about forty seconds. The cured mixture forms the mixture inlay in the manner described before.

The crown 44 is removed from the tooth along with the mixture inlay. Any uncured mixture inside the metal coping is wiped out with a suitable instrument. Contouring and removal of flash then can be accomplished with a sandpaper disc or clean stone held parallel to the external contour of the crown.

Preferably the crown 44 and mixture inlay once again is inserted on the tooth 46. Additional, corrections then can be made, if necessary, by adding more mixture and repeating the above steps to cure the mixture and form the mixture inlay.

When the desired contour has been obtained, the crown 44 along with the mixture inlay is removed and light is applied to all surfaces of the additional mixture to insure complete hardening. The crown along with the mixture inlay then is heated in an oven at about 620° C. to burn out and release the resin binding agent. The crown and mixture inlay then are heated to the fusion temperature of the porcelain in the mixture inlay and, in this instance, at a temperature of about 920° C. to fuse the porcelain in the mixture and form the ceramic core.

After the ceramic core and crown has been cooled, a creamy mixture of low-fusing glaze can be applied to the external surface of the ceramic core to fill any porosity and produce a smooth surface. Also, stains can be added to the glaze if desired. It should be noted that no stain or glaze should extend onto the surface of the ceramic core which will be in contact with the tooth 46.

The crown 44 along with the ceramic core then is returned to the oven, and the crown is fired at 880° C. It is then removed from the oven, cooled and the metal polished. The corrected crown with the ceramic core is tried in the mouth for final approval. If satisfactory, the tooth 46 is cleansed of any remaining trace of separating agent with a degreasing agent and the crown 44 with the ceramic core is cemented onto the tooth 46.

It should be noted that care must be taken not to contaminate the mixture with blood. A cervical clamp or retraction cord can be placed for better access to the cavity 50, but astringents containing heavy metals which might discolor the porcelain in the mixture should be avoided.

Also, it should be noted that variation of the above technique can be used on any type of ceramic crown, not only to refine margins or cavities, but to add bulk wherever needed.

Shown in FIGS. 9, 10 and 11 are three modified frameworks 26a, 26b and 26c. The frameworks 26a, 26b and 26c are constructed exactly like the framework 26 described in detail before, except the framework 26a, 26b and 26c each have a modified base 30a, 30b and 30c respectively. Each of the modified bases 30a, 30b and 30c is designed and shaped or contoured to be utilized with a different shape or class of cavity as compared with the particular cavity shown in FIGS. 1, 2, 4 and 6. In each instance, the base is shaped generally to conform to the overall shape of the cavity so the base functions to fill a portion of cavity and to provide additional structural integrity to the final porcelain inlay and to reduce the presence of binding agent.

It should be noted that the framework 26 or 26a or 26b or 26c could be constructed to include only the base and no handle which may be desirable in some applications.

The present invention also contemplates a kit for use by dentists in preparing porcelain inlays in a cavity in a patient's mouth. The kit would include a supply of heat fusable porcelain and a supply of a binding agent suitable for mixing with the heat-fusable porcelain so that the mixture comprising the porcelain and the binding agent would cure within a period of time to form the mixture inlays capable of retaining the general shape formed in the cavity in the tooth in the case of a chemically curing mixture. The mixture inlay would be heated to form the ceramic core in the manner described before with respect to the ceramic core 34. The supply of porcelain and the supply of binding agent also would be mixable to form the corrective layer which then could be heated to form the corrective ceramic layer in the manner described before with respect to the corrective ceramic layer 40.

In one embodiment, a second supply of porcelain and a second supply of binding agent may be supplied in the kit for forming the corrective layer. This supply of porcelain would have a fusion temperature less than the fusion temperature of the porcelain used to make the ceramic core. In this instance, the binding agent may be a resin which is light curable with the porcelain for making a corrective layer which is light curable.

The kit contemplated by the present invention also would include the frameworks 26, 26a, 26b and 26c which are disposable in the mixture so a portion of the handle 28 extends from the mixture inlay to faciltate the removal and insertion of the mixture inlay and the resulting ceramic core in the manner described before.

Changes may be made in the construction and operation of the various parts, elements and assemblies described herein and in the steps or in the sequence of steps of the methods described herein without departing from the spirit and scope of the invention as defined in the following claims.

I claim:

1. A method for filling a cavity in a tooth in a patient's mouth with a porcelain inlay formed directly from the cavity, comprising the steps of:
    preparing a mixture comprising a porcelain and a binding agent;
    disposing the mixture in the cavity in a quantity sufficient to fill at least a portion of the cavity;
    permitting the mixture to cure in the cavity to form a mixture inlay which substantially will retain the shape formed in the cavity;
    removing the mixture inlay from the cavity;
    heating the mixture inlay for a sufficient time and at a sufficient temperature to heat fuse the mixture inlay to form a ceramic core;
    placing the ceramic core in the cavity;
    preparing a corrective layer comprising a porcelain and binding agent;
    disposing the corrective layer about the ceramic core and about the cavity in the cavity to fill at least portions of any gap between the ceramic core and the cavity;
    permitting the corrective layer to cure in the cavity to form a cured corrective layer which substantially will retain the shape formed in the cavity and which is bonded to the ceramic core;
    removing the cured corrective layer with the ceramic core bonded thereto from the cavity;
    heating the cured corrective layer for a sufficient time and at a sufficient temperature to heat fuse the porcelain in the cured corrective layer and form a corrective ceramic layer bonded to the ceramic core; and
    securing the corrective ceramic layer with the ceramic core bonded thereto in the cavity.

2. The method of claim 1 wherein the step of preparing the corrective layer is further defined to comprise selecting the binding agent from a group of resins suitable for use in the patient's mouth.

3. The method of claim 1 wherein the step of preparing the corrective layer is defined further to comprise:
    selecting a porcelain with a lower fusion point than the fusion point of the porcelain in the ceramic core.

4. The method of claim 3 wherein the step of heating the cured corrective layer and forming the corrective ceramic layer is defined further to comprise the steps of:
    heating the cured corrective layer with the ceramic core bonded thereto at a temperature below a fusion temperature of the cured corrective layer and at a temperature high enough and for a sufficient period of time to release a substantial portion of the binding agent from the cured corrective layer; and
    heating the cured corrective layer at a temperature at least equal to the fusion temperature of the porcelain in the cured corrective layer and below the fusion temperature of the ceramic core for a period of time sufficient to fuse the porcelain in the cured corrective layer and form the corrective ceramic layer.

5. The method of claim 1 further comprising the step of:
    removing a portion of excess binding agent from the corrective layer in the cavity before permitting the corrective layer to cure in the cavity.

6. The method of claim 1 wherein the step of preparing the corrective layer is defined further to comprise selecting a binding agent to mix with the porcelain in the corrective layer which will cause the corrective layer to cure chemically with the passage of time; and
    wherein the step of permitting the corrective layer to cure is defined further to comprise the step of:
    allowing the passage of a period of time sufficient for the corrective layer to cure.

7. The method of claim 1 wherein the step of preparing the corrective layer is defined further to comprise selecting a binding agent to mix with the porcelain in the corrective layer which will cause the mixture to cure when light is applied thereto; and wherein the step of permitting the mixture to cure is defined further to comprise the step of:
    applying light to the mixture for a sufficient period of time to cure the corrective layer and form the cured corrective layer.

8. The method of claim 1 further comprising the step of:
    securing the corrective ceramic layer with the ceramic core bonded thereto in the cavity.

9. The method of claim 1 wherein the step of disposing the corrective layer about the ceramic core and about the cavity is defined further to comprise the steps of:
    disposing the corrective layer in the cavity before placing the ceramic core in the cavity;
    placing the ceramic core in the cavity and generally on the corrective layer with the corrective layer substantially filling the gap between the ceramic core and the cavity; and
    disposing the corrective layer generally over an outer surface of the ceramic core so the corrective layer substantially encompasses the ceramic core.

10. The method of claim 1 wherein the step of disposing the corrective layer about the ceramic core and about the cavity is defined further to comprise the steps of:

disposing the corrective layer in at least portions of the cavity and generally about an outer surface of the ceramic core after placing the ceramic core in the cavity, the corrective layer substantially encompassing at least portions of the ceramic core generally near the outer surface of the tooth.

11. A kit for use in preparing dental inlays for filling cavities in a tooth in a patient's mouth, comprising:

a first supply of porcelain;

a first supply of binding agent suitable for mixing with the porcelain to form a mixture which is disposable in the cavity in the patient's mouth and curable to form a mixture inlay which substantially will retain the shape formed in the cavity, the mixture being capable of being heated to a sufficient temperature and for a sufficient period of time to heat fuse the porcelain in the mixture and form a ceramic core;

a second supply of porcelain having a fusion temperature lower than the first porcelain; and a second supply of binding agent for mixing with the second supply of porcelain to form a corrective layer which is disposable generally in the cavity in the patient's mouth and generally about the ceramic core and curable to form a cured corrective layer which substantially will retain the shape formed in the cavity, the cured corrective layer being capable of being heated to a sufficient temperature and for a sufficient period of time to heat fuse the second supply of porcelain in the cured corrective layer to form a corrective ceramic layer and being bonded to the ceramic core.

12. The kit of claim 11 wherein the binding agent is defined further as being suitable to form the corrective layer which is light curable to form the cured corrective layer.

13. The kit of claim 11 in which the first supply of porcelain the first supply of binding agent are disposed in a container and the second supply of porcelain and the second supply of binding agent are disposed in a container.

* * * * *